US006001332A

United States Patent [19]
Garrett

[11] Patent Number: 6,001,332
[45] Date of Patent: *Dec. 14, 1999

[54] MEDICAL GAS MIXTURE

[75] Inventor: Michael E. Garrett, Surrey, United Kingdom

[73] Assignee: The BOC Group plc, Surrey, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/053,803

[22] Filed: Apr. 2, 1998

Related U.S. Application Data

[63] Continuation of application No. 08/600,789, Feb. 13, 1996, abandoned.

[30] Foreign Application Priority Data

Feb. 16, 1995 [GB] United Kingdom .................. 95 02987
Apr. 4, 1997 [GB] United Kingdom .................. 97 06817

[51] Int. Cl.$^6$ .......................... A61K 49/00; A61K 47/00; A61B 5/055; A61B 5/0265; C09K 3/00
[52] U.S. Cl. .................... 424/9.3; 128/653.2; 128/653.4; 252/372; 424/613; 514/789; 514/826; 514/958; 514/959

[58] Field of Search ...................... 514/789, 826, 514/959, 958; 424/9.3, 613; 128/653.2, 653.4; 252/372

[56] References Cited

U.S. PATENT DOCUMENTS

| | | | |
|---|---|---|---|
| 3,974,830 | 8/1976 | LaVerne | 128/203.27 |
| 4,989,597 | 2/1991 | Werner | 128/203.12 |
| 5,271,401 | 12/1993 | Fishman | 128/654 |

FOREIGN PATENT DOCUMENTS

WO 93/06869  4/1993  WIPO .......................... A61K 49/00

*Primary Examiner*—Jose' G. Dees
*Assistant Examiner*—Marina Lamm
*Attorney, Agent, or Firm*—Philip H. Von Neida; Salvatore P. Pace

[57] ABSTRACT

A medical gas mixture which comprises from 20 to 70% oxygen, from 1 to 10% carbon dioxide and the balance, except for incidental constituents not adversely affecting the basic properties of the gas mixture, being helium. The subject mixtures are useful in the treatment of asthma and in enhancing magnetic resonance imaging.

12 Claims, No Drawings

MEDICAL GAS MIXTURE

RELATED APPLICATIONS

This application is a continuing application under 37 C.F.R.§ 1.53(b) of U.S. patent application Ser. No. 08/600,789 filed Feb. 13, 1996 now abandoned.

FIELD OF THE INVENTION

This invention relates to medical gas mixtures and, more particularly, to such mixtures for use in the treatment of chronic obstructive airway disease, asthma, various other medical conditions, and particularly for magnetic resonance imaging (MRI).

BACKGROUND OF THE INVENTION

During an acute asthma attack, there is a marked exacerbation of the underlying inflammation in the small and medium sized airways in the lungs. The lining of the airways becomes edematous, and the surrounding smooth muscle contracts. The transmission of air becomes restricted and turbulent resulting in ventilation/perfusion (V/Q) mismatching and hypoxemia.

Acute asthma attacks are often initially treated with an inhaled beta adrenergic agonist that simulates the β-receptors on airway smooth muscles causing bronchodilatation. However, β-agonists do not treat the underlying inflammation and, as the asthma attack develops, the β-receptors tend to become refractory to β-agonist medication. Acute asthma also causes hypoxemia which is conventionally treated with oxygen. Hypoxemia is often associated with increased bronchospasm, bronchia reactivity and anxiety, all of which can be ameliorated with oxygen therapy.

The initial effect of β-agonist medication in an acute asthma attack is to cause the pulmonary vasculature to dilate which tends to exacerbate the edema. This results in a further deterioration in the V/Q mismatching and hypoxemia. As a general rule, a β-agonist medication should always be given with oxygen in an acute asthma attack. Currently, oxygen is administered under medical supervision. It would obviously be beneficial for patients, for example asthmatics, to be able to self-administer oxygen at the onset of an attack so as to optimize their treatment. However, for patients with chronic obstructive airway disease, high partial pressure of oxygen can compromise their hypoxic drive.

It is known to administer a helium-oxygen gas mixture in obstructive airways disease. The usefulness of helium in such conditions is related to its physical properties. It is an inert gas without any pharmacological activity. It has a lower density than nitrogen or oxygen so that, when is mixed with oxygen, there results a lower airways resistance than with either oxygen alone or an oxygen-nitrogen mixture. The Reynold's number is reduced such that areas of turbulent flow in the inflamed airways are converted to laminar flow.

In the distal airways, the low solubility of helium prevents any significant absorption into the pulmonary vasculature. This prevents atelectasis formation that can occur with 100% oxygen (peripheral lung collapse). There is laminar flow in the distal airways that is dependent on the viscosity of the inhaled gas. Although helium is relatively viscous compared to oxygen or nitrogen, there is still a net gain in overall gas flow in acute asthma using a helium oxygen mix.

A helium:oxygen mixture of 80:20 volume percent has been shown to reduce pulses paradoxus and increase peak expiratory flow in patients with acute asthma. This reduces muscle fatigue, maintains arterial oxygenation and keeps the patient in relatively good condition until other forms of medication have had the opportunity to exert their effect. An additional benefit of a helium oxygen mixture is that when administered to patients with an acute myocardial infarction the myocardium appears to be stabilized reducing the risk of ventricular arrhythmias.

Another important benefit of oxygen is that, in MRI detection of cancer, the presence of oxygenated blood within the tumor can commonly improve the MRI imaging. This can be achieved in particular by having the patient inhale an enhanced level of oxygen. In addition, it has been found that the presence of carbon dioxide in the inhaled gas acts as a vasodilator in those blood vessels in and around the tumor thereby facilitating an increased level of oxygen in such vessels which acts to improve imaging. Typically, five volume percent of carbon dioxide ($CO_2$) is added to the gas, although somewhat higher or lower concentration may be used to good effect in different circumstances.

While carbon dioxide can be administered in air or oxygen-enriched air, it is more commonly administered in admixture with pure oxygen. Such 5/95 vol. percent mixtures carbon dioxide and oxygen are commercially available. However, a problem inherent in such preparations is the pronounced physiological effects of a 5% $CO_2$ concentration, including inability to breath normally, high ventilation rates, panic and production of heat which may lead to the patient being unable or unwilling to continue with the imaging or treatment. This is particularly troublesome for patients with obstructive pulmonary disease.

It has been recently proposed to reduce the carbon dioxide concentration in such preparations to 4 vol%, possibly 3 vol% and perhaps below in order to minimize such detrimental physiological effects without substantial loss of the benefits in the imaging process. The reduction in such effects must, however, be balanced against the need to obtain the best possible imaging.

Therefore, there is a need for a gas mixture which can be made readily available to all patients for self administration, for example at the onset of an acute asthma attack, or for use in imaging, for example magnetic resonance imaging (MRI) or for general medical use, and which can overcome the above difficulties.

SUMMARY OF THE INVENTION

In accordance with the invention, there is provided a medical gas mixture which comprises, by volume, from about 20% to 70% oxygen, from about 1% to 10% carbon dioxide and the balance, except for incidental constituents not adversely affecting the basic properties of the gas mixture, being helium.

DETAILED DESCRIPTION OF THE INVENTION

Unless otherwise stated, all gas percentages in this specification and in the claims are by volume. The medical gas mixtures of the present invention comprise from about 20% to 70% oxygen, from about 1% to 10% carbon dioxide and the balance, except for incidental constituents not adversely affecting the basic properties of the gas mixture, being helium. The oxygen component is preferably from about 20% to 40% and more preferably 25 to 35% oxygen. For the most effective treatment of asthma the compositions of the invention contain from about 30% to 35% oxygen. For use in imaging (MRI), the oxygen content is preferably from about 25% to 30% as no higher arterial oxygen concentration is introduced above such amounts in the mixture.

The carbon dioxide component of the subject medical compositions is preferably from about 3% to 7%. For treatment of asthma, the compositions of the invention contain from about 3% to 5% carbon dioxide. For use in imaging (MRI), the carbon dioxide content is preferably from about 1% to 5%, preferably from about 1% to 4%, and most preferably from about 1% to 3%.

Although it is known that the administration of a small amount of carbon dioxide has a number of useful pharmacological actions, for example it is potent stimulus for respiration and the natural presence in a person's exhaled breath performs that action, its role in the stated amounts in the gas mixture of the invention has been shown to be especially critical. Carbon dioxide is also a bronchodilator. In imaging, carbon dioxide in the gas mixture acts as a vasodilator, allowing for a greater concentration of oxygen in to the blood in the vicinity of the tumor in particular.

The effect of helium in the subject compositions is to greatly reduce the "drag" in a patient's lungs resulting from the high breathing rate triggered by the carbon dioxide constituent and at the same time to improve the perfusion of the inhaled gas constituents—oxygen and carbon dioxide—into the depths of the lungs. The presence of helium, therefore, facilitates the use of somewhat lower carbon dioxide concentration than the typical 5% content in the commercial mixtures. Helium is preferably present in the gas mixture in an amount of at least 60 vol% in order to achieve optimum flow dynamics in the patient to be improved. Preferably, the helium content of the gas mixture is at least 65 vol%.

The lower concentration of oxygen in the gas mixtures of the present invention as compared to the commercial mixtures referred to above may also be beneficial in reducing oxygen saturation in the plasma of the blood, thereby improving the oxyhemoglobin image in MRI in particular.

An overall preferred gas mixture contains from 25 to 35% oxygen, 1 to 3% carbon dioxide and the balance being helium. A preferred mixture for MRI imaging consists of about 30% oxygen, 2% carbon dioxide and 68% helium. Experiments have shown that, in the mixtures of the invention, the use of the relatively low levels of carbon dioxide, particularly less than about 3%, surprisingly does not decrease its vasodilation effects in comparison with the commercial mixtures containing 5%. Further, the comparatively reduced level of carbon dioxide neither adversely affects the overall effectiveness of the imaging or willingness or ability of patients to continue to inhale the gas mixture.

For use by asthmatics, a gas mixture containing 33 to 35% oxygen, 3 to 5% carbon dioxide and the balance helium is particularly preferred. In addition, the experiments confirm that the gas mixture of the invention is more readily and comfortably inhaled than an equivalent helium-free mixture.

The basic properties exhibited by the gas mixture of the invention, namely good blood oxygenation and vasodilation in the patient inhaling the mixture together with easier breathing characteristics for the patient, allows the mixture to be used to good effect not only for enhanced imaging procedures and results but also in the associated treatment of the tumors themselves.

In this latter regard, it has surprisingly been found that the gas mixture of the invention can greatly assist in the chemotherapy and radiotherapy treatment of tumors. In particular, the improved imaging effects afforded by the mixture based in the presence of enhanced levels of oxygen can show more clearly those tumors and parts of tumors in which blood is still flowing, i.e. have not been necrotic, and that are therefore susceptible to chemotherapy and/or radiology. Furthermore, the vasodilatory properties of the gas mixtures of the invention allow, during inhalation by the patient, for the chemotherapy and/or radiotherapy drugs to be more widely available within the tumor in particular and to be retained or trapped in the tumor once inhalation has ceased and the blood vessels constrict.

The invention can therefore be regarded as the use of the gas mixture of the invention not only, inter alia ,in tumor imaging techniques, but also in the associated treatments of the tumors.

I claim:

1. A medical gas mixture consisting essentially of, by volume, from about 20% to 70% oxygen, from about 1% to 10% carbon dioxide and the balance helium.

2. A medical gas mixture in accordance with claim 1 consisting essentially of, by volume, from about 20% to 40% oxygen, from about 2% to 10% carbon dioxide and the balance being helium.

3. A medical gas mixture in accordance with claim 2 consisting essentially of, by volume, from about 30% to 35% oxygen, from about 3% to 7% carbon dioxide and the balance helium.

4. A medical gas mixture in accordance with claim 1 useful, by inhalation, in enhancing magnetic resonance imaging in a patient consisting essentially of, by volume, from about 25% to 30% oxygen, from about 1% to 5% carbon dioxide and the balance helium.

5. A medical gas mixture in accordance with claim 4 consisting essentially of, by volume, from about 25% to 30% oxygen, from about 1% to 3% carbon dioxide and the balance helium.

6. A medical gas mixture in accordance with claim 1 useful, by inhalation, in the treatment of asthma in a patient consisting essentially of, by volume, from about 30% to 35% oxygen, from about 3% to 5% carbon dioxide and the balance helium.

7. A medical gas mixture in accordance with claim 6 consisting essentially of, by volume, from about 33% to 35% oxygen, from about 3% to 5% carbon dioxide and the balance helium.

8. A medical gas mixture in accordance with claim 1 containing no less than 60 volume percent of helium.

9. A medical gas mixture in accordance with claim 1 containing no less than 65 volume percent of helium.

10. A method of enhancing magnetic resonance imaging in a patient undergoing such imaging comprising causing the patient to inhale the gas mixture of claim 4.

11. A method in accordance with claim 10, wherein said gas mixture consisting essentially of, by volume, from about 25% to 30% oxygen, from about 1% to 3% carbon dioxide and the balance helium.

12. A method of treating asthma comprising causing a patient in need of such treatment to inhale the gas mixture of claim 6.

* * * * *